United States Patent [19]

Slocum

[11] Patent Number: Plant 5,799

[45] Date of Patent: Nov. 11, 1986

[54] LOTUS PLANT CV ANGEL WINGS

[76] Inventor: Perry D. Slocum, 191 Leatherman Gap Rd., Franklin, N.C. 28734

[21] Appl. No.: 789,311

[22] Filed: Oct. 18, 1985

[51] Int. Cl.[4] ..... A01H 5/00

[52] U.S. Cl. ..... Plt./68

[58] Field of Search ..... Plt./68

*Primary Examiner*—Robert E. Bagwill

[57] ABSTRACT

A novel lotus plant having white blossoms borne high above large leaves with convoluted edging.

5 Drawing Figures

The present invention relates to a new and distinct variety of lotus plant named Angel Wings of the decorative class which was originated by Perry D. Slocum, by crossing a *Nelumbo nucifera,* variety: *Shirokunshi* with a *Nelumbo nucifera,* variety: *Rubrum.*

The primary objective of this breeding was to produce a new and improved lotus variety having a colorful white flower which was hardy with the flowers extending substantially above the leaves. This objective was achieved along with other desirable improvements as evidenced by the unique combination of characteristics which are outstanding in the new variety and which distinguish it from all other lotus varieties by its:

(1) flowers of substantially white petals with green tinted lower petals;

(2) leaves have large convolutions along the edges; and (3) flower petals curled inwardly.

Asexual reproduction of the new variety which was performed at Franklin, N.C., by tuber division shows that the foregoing characteristics and distinctions come true to form and are established and transmitted through succeeding propagations.

The accompanying photographs show typical specimens of the leaf, stem, bud and flowers of the new lotus variety in different stages of development and as depicted in color as nearly true as is reasonably possible to make the same in color photographs of this character.

The following is a detailed description of the new variety, with color terminology in accordance with *Exotica,* 8th Edition, published by Roehrs Company, Inc. of New Jersey, Horticultural Color Guide:

Parentage: Seedling.

*Seed parent.—Nelumbo nucifera,* variety: *Shirokunshi.*

*Pollen parent.—Nelumbo nucifera,* variety: *Rubrum.*

Classification: Decorative.

Height: Leaves are approximately 4 feet above water with a 16–23 inch diameter leaves with flowers approximately 10–12 inches above leaves.

Location where grown and observed: Outdoors in water pools in Franklin, N.C. from June 20 to September 10.

Cold resistance: Hardy perennial.

Blooming period: In Franklin, N.C. climatic area, blooming begins in June and continues through September.

SEED POD

Non-distinguishable seed pod resembles other lotus plant seed pods.

FLOWER

Figure 2:
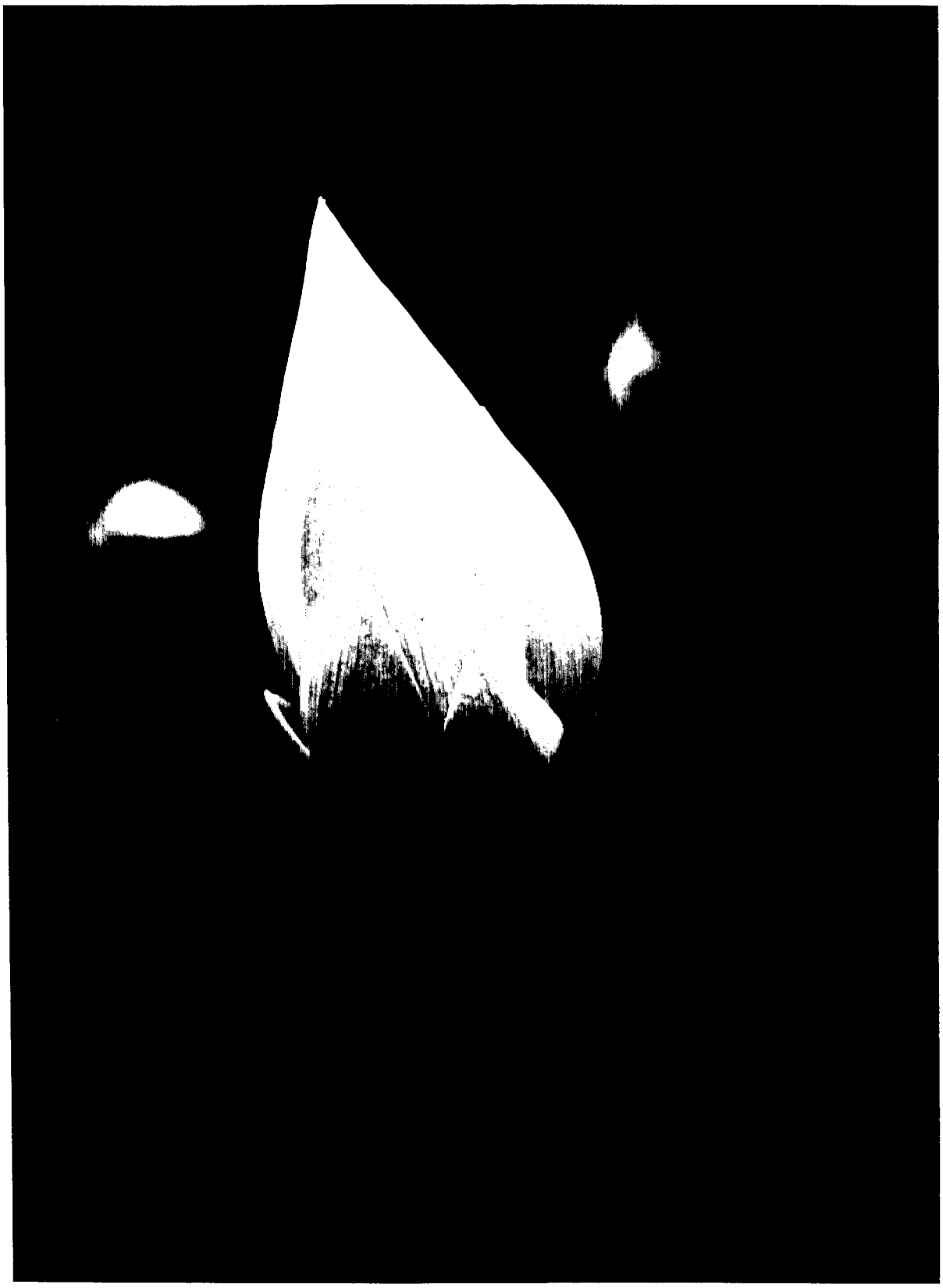

Bud:

*Color as shown in* FIG. 2.—Upper bud petals have #25 scarlet tips with #79 citron body portion. Lower bud petals are #74 paris green with a peduncle of #70 ivy green.

Figure 3:
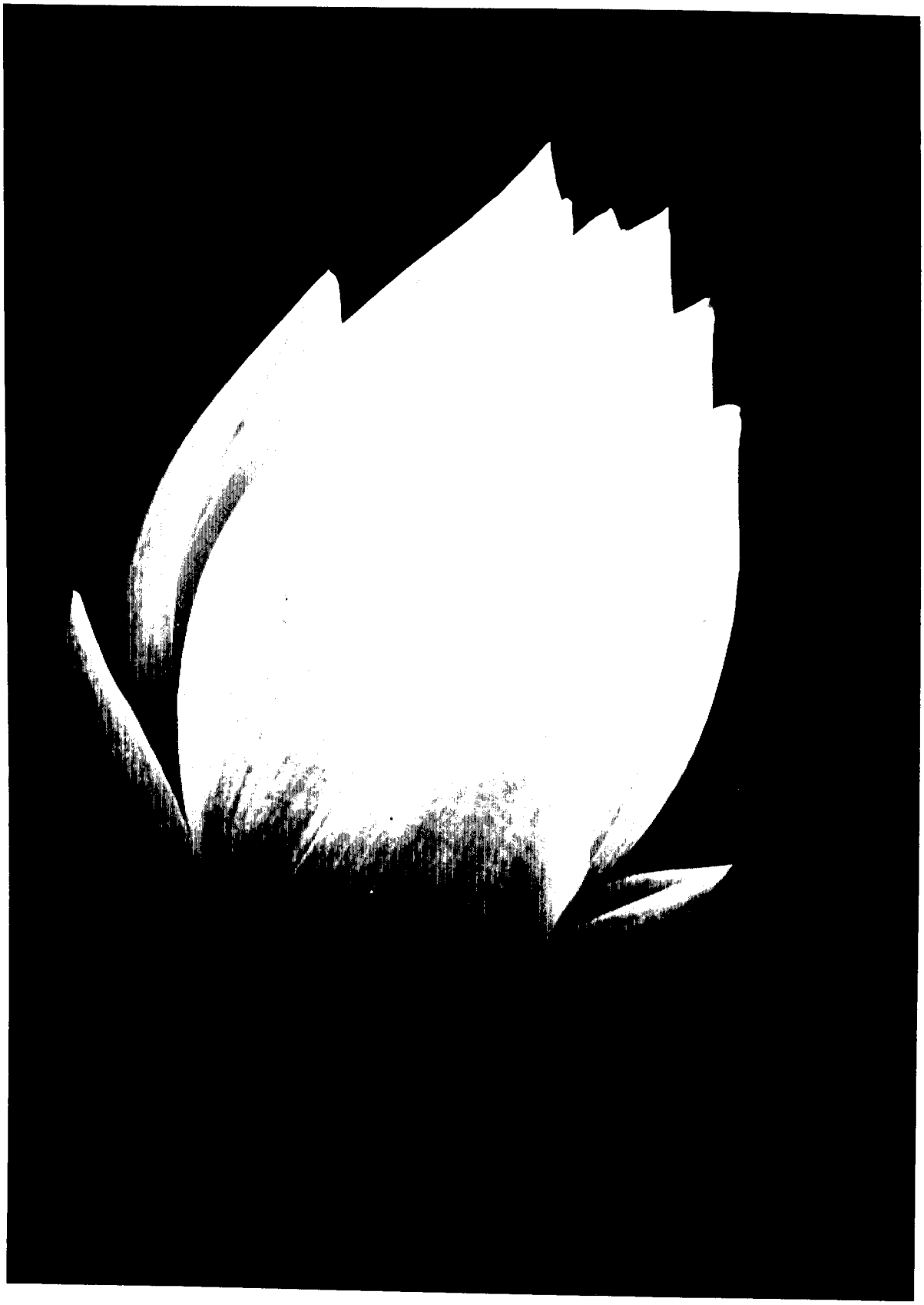

*When petals first divide* (FIG. 3).—Uppermost petals are slightly whiter than #1 cream with #25 scarlet tips. Middle petals approximate #72 spring green with the bottom petals being #73 grass green.

Bloom:

*Size.*—8 to 10 inches in diameter.

*Stem.*—Stiff, strong #76 meadow green in color.

Figure 5:
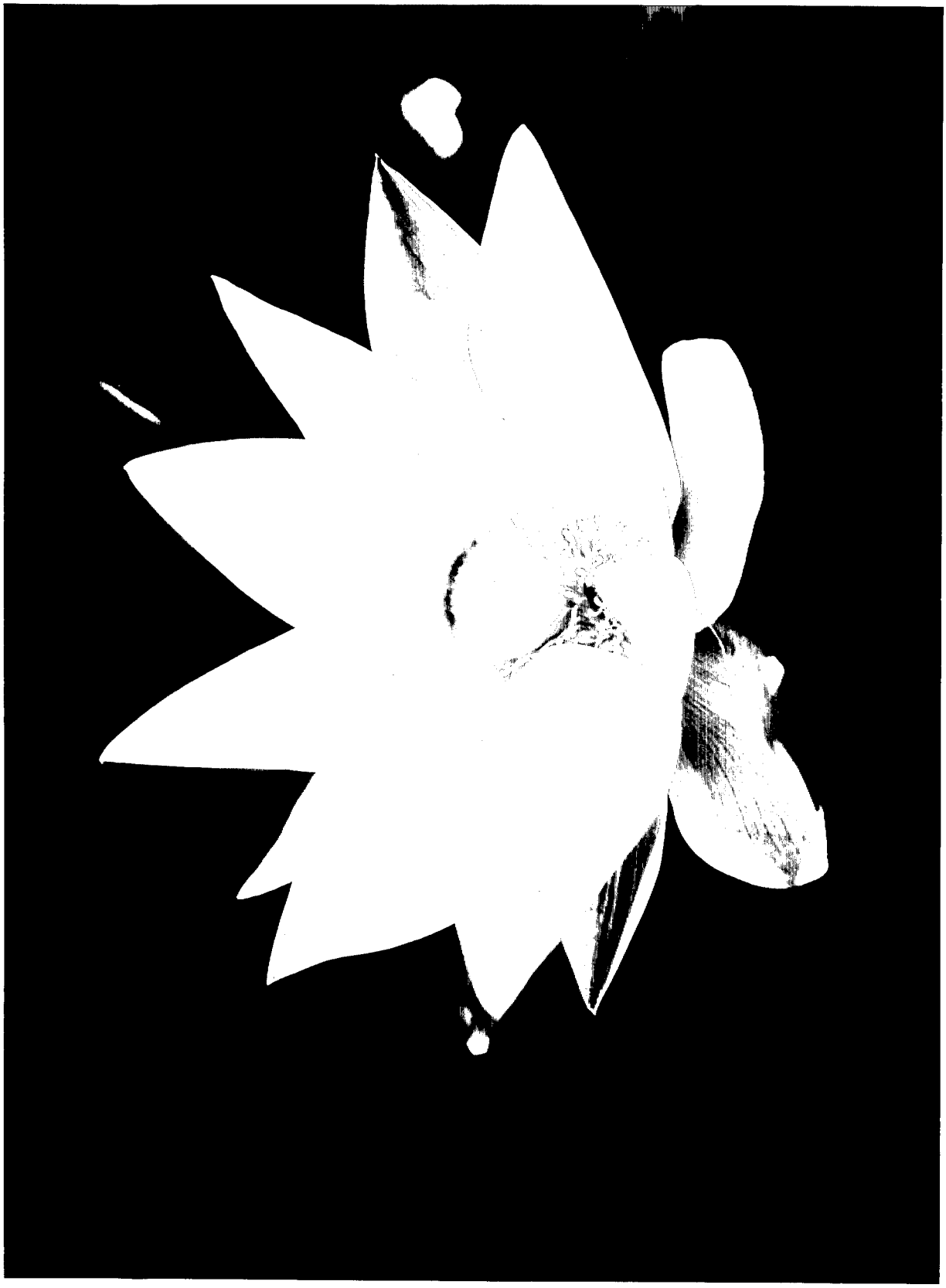
Figure 4:
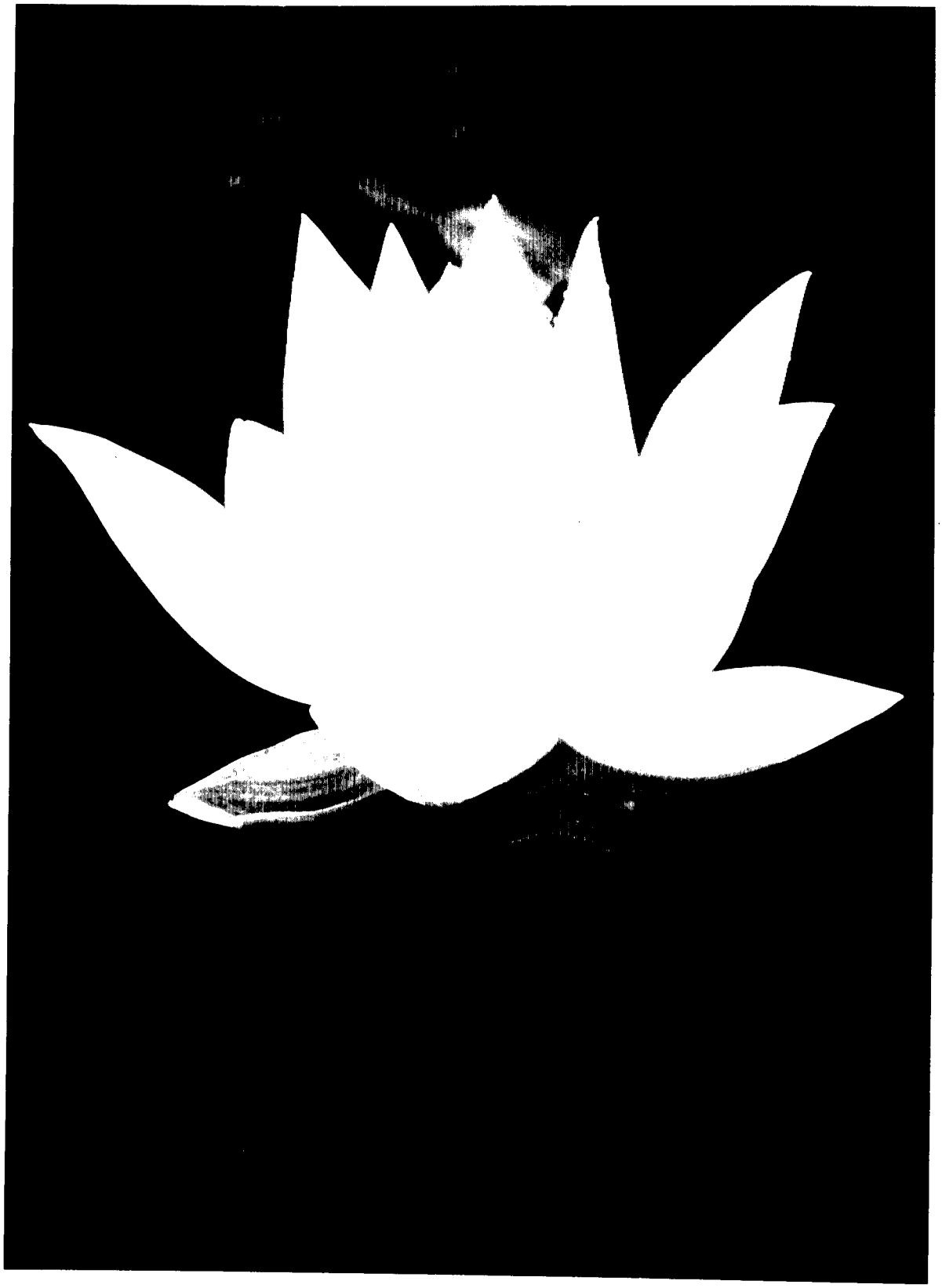

*Form.*—First day flowers are cup shaped, second and third days flowers are fully opened (FIGS. 4 and 5).

*Petalage.*—Usually about 18.

*Color.*—Center of flower — Center of pistils #4 buttercup yellow at the pistil edge #72 spring green with anthers slightly whiter than #1 cream and stamens #4 buttercup yellow. Outer petals are between #78 chartreuse and 190 79 citron with the inner petals being whiter than #1 cream.

*Petals.*—Texture — smooth.

*Fragrance.*—Very fragrant resembling anise.

PLANT

Form: All branching of the plant is done under water.

Growth: Medium about 4 feet above water.

Foliage:

*Size.*—16–23 inch diameter leaves.

*Quantity.*—Plentiful.

*Color.*—#70 Ivy green.

Figure 1:
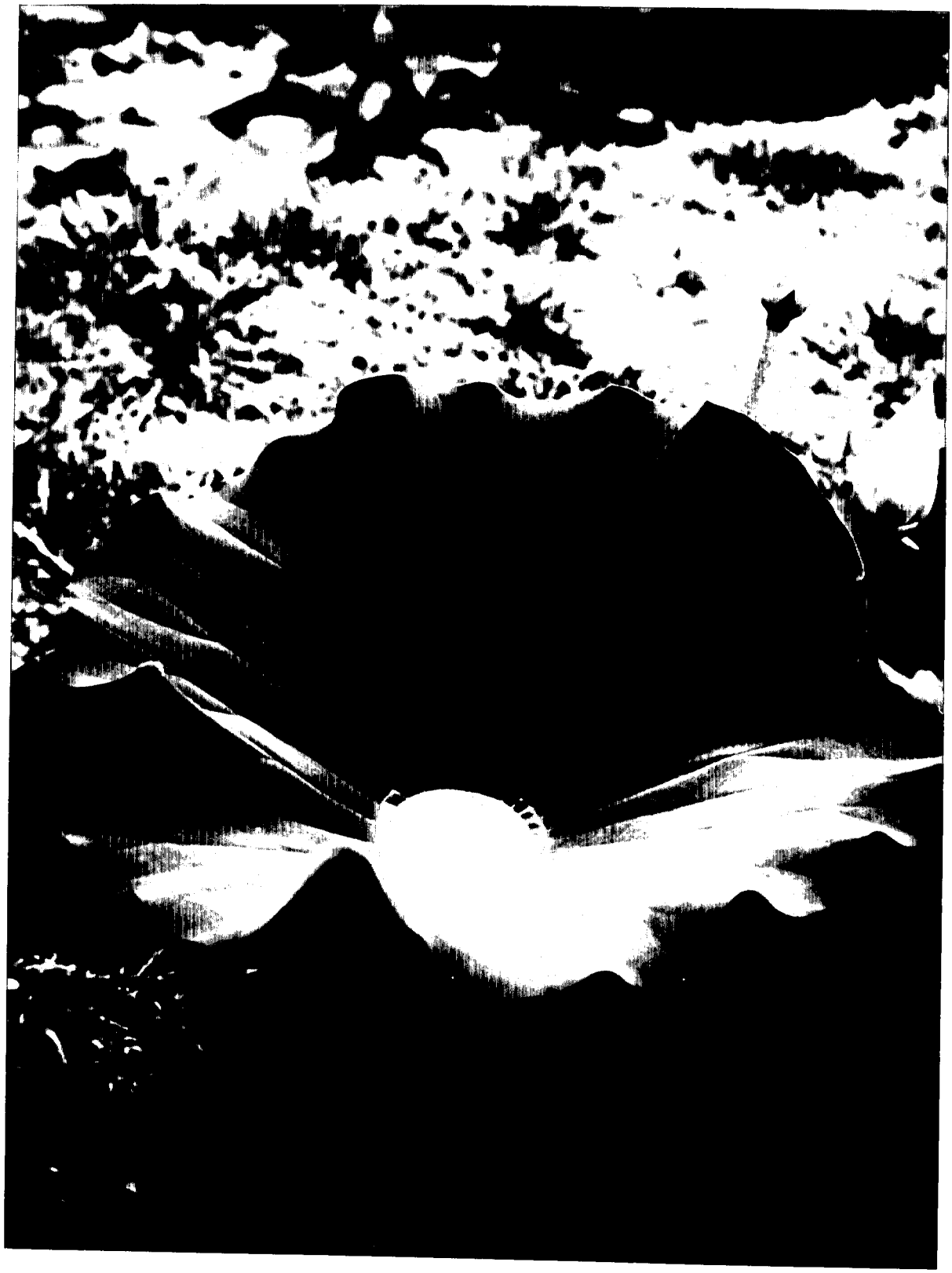

*Texture.*—Convoluted edges with smooth leaves as shown in FIG. 1.

I claim:

1. A new and distinct variety of lotus plant substantially as herein shown and described.

* * * * *